(12) United States Patent
Motohara et al.

(10) Patent No.: US 10,321,805 B2
(45) Date of Patent: Jun. 18, 2019

(54) IMAGING UNIT, IMAGING MODULE, AND ENDOSCOPE

(71) Applicant: OLYMPUS CORPORATION, Tokyo (JP)

(72) Inventors: Hiroyuki Motohara, Hachioji (JP); Yasuhiro Kusano, Yabuki-machi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/860,884

(22) Filed: Jan. 3, 2018

(65) Prior Publication Data

US 2018/0125335 A1 May 10, 2018

Related U.S. Application Data

(63) Continuation of application No. PCT/JP2017/002065, filed on Jan. 23, 2017.

(30) Foreign Application Priority Data

Jan. 28, 2016 (JP) ................. 2016-014339

(51) Int. Cl.
*H04N 5/225* (2006.01)
*A61B 1/00* (2006.01)
(Continued)

(52) U.S. Cl.
CPC ........ *A61B 1/00096* (2013.01); *A61B 1/0011* (2013.01); *A61B 1/04* (2013.01);
(Continued)

(58) Field of Classification Search
CPC .... H04N 5/225; H04N 5/2251; H04N 5/2253; H04N 5/2254; H04N 5/2257
(Continued)

(56) References Cited

U.S. PATENT DOCUMENTS 6,319,196 B1 11/2001 Minami
8,085,334 B2 12/2011 Itakura
(Continued)

FOREIGN PATENT DOCUMENTS

| JP | H11-076156 A | 3/1999 |
| JP | 2000-019427 A | 1/2000 |
| JP | 2010-051538 A | 3/2010 |

OTHER PUBLICATIONS

International Search Report dated Mar. 7, 2017 issued in PCT/JP2017/002065.

*Primary Examiner* — Anthony J Daniels
(74) *Attorney, Agent, or Firm* — Scully, Scott, Murphy & Presser, PC.

(57) ABSTRACT

An imaging unit includes: an optical system; a semiconductor package including an image sensor, and a connection electrode formed on a back surface; a cable; an electronic component; and a multi-layer substrate having a rectangular plate shape and including: a first electrode and a second electrode arranged side-by-side with each other on a front surface, the semiconductor package being mounted on the first electrode, and the cable being connected to the second electrode; and a third electrode on a back surface, the electronic component being mounted on the third electrode. The multi-layer substrate includes walls on at least two opposing sides of the back surface, and the semiconductor package is disposed such that a light receiving surface of the image sensor is arranged horizontally with respect to the multi-layer substrate.

9 Claims, 14 Drawing Sheets

(51) Int. Cl.
*A61B 1/04* (2006.01)
*G02B 23/26* (2006.01)
*H01L 27/14* (2006.01)
*A61B 1/06* (2006.01)
*A61B 1/05* (2006.01)
*A61B 1/005* (2006.01)
*G02B 23/24* (2006.01)
*H01L 27/146* (2006.01)

(52) U.S. Cl.
CPC ............... *A61B 1/051* (2013.01); *A61B 1/06* (2013.01); *G02B 23/26* (2013.01); *H01L 27/14* (2013.01); *H04N 5/2251* (2013.01); *H04N 5/2253* (2013.01); *A61B 1/005* (2013.01); *A61B 1/00006* (2013.01); *A61B 1/00009* (2013.01); *A61B 1/00045* (2013.01); *A61B 1/00105* (2013.01); *G02B 23/24* (2013.01); *H01L 27/14618* (2013.01); *H04N 2005/2255* (2013.01)

(58) Field of Classification Search
USPC ........................................................ 348/374
See application file for complete search history.

(56) References Cited

U.S. PATENT DOCUMENTS

| 2002/0044215 | A1* | 4/2002 | Takagi | H01L 25/16 348/374 |
| 2005/0099531 | A1* | 5/2005 | Wu | H01L 247/14618 348/374 |
| 2008/0303939 | A1* | 12/2008 | Hsu | H01L 27/14618 348/374 |
| 2009/0033789 | A1* | 2/2009 | Lin | G02B 7/02 348/374 |
| 2009/0033790 | A1* | 2/2009 | Lin | G02B 7/023 348/374 |
| 2011/0102667 | A1* | 5/2011 | Chua | H04N 5/2251 348/374 |
| 2011/0249106 | A1* | 10/2011 | Makino | H04N 5/2254 348/76 |
| 2011/0285890 | A1* | 11/2011 | Choi | H04N 5/2251 348/308 |
| 2012/0068324 | A1* | 3/2012 | Hoshi | A61B 1/0011 257/680 |
| 2012/0133825 | A1* | 5/2012 | Nakajima | H04N 5/2253 348/374 |
| 2016/0205296 | A1* | 7/2016 | Igarashi | A61B 1/0008 348/76 |

* cited by examiner

IMAGING UNIT, IMAGING MODULE, AND ENDOSCOPE

CROSS-REFERENCE TO RELATED APPLICATION

This application is a continuation of PCT international application Ser. No. PCT/JP2017/002065 filed on Jan. 23, 2017 which designates the United States, incorporated herein by reference, and which claims the benefit of priority from Japanese Patent Applications No. 2016-014339, filed on Jan. 28, 2016, incorporated herein by reference.

BACKGROUND

The present disclosure relates to an imaging unit, an imaging module, and an endoscope.

In the related art, endoscope apparatuses are widely used for various examinations in medical and industrial fields. Among these, medical endoscope apparatuses are widely used because its capability of obtaining in-vivo images inside the body cavity of a subject such as a patient without performing incision on the subject by inserting in the body cavity of the subject a flexible insertion section having an elongated shape including an image sensor provided at its distal end, and its capability of further performing treatment procedure by allowing a treatment instrument to be projected from the distal end of the insertion section as necessary.

At the distal end of the insertion section of such an endoscope apparatus, an imaging unit including an image sensor and a circuit board on which electronic components such as a capacitor and an IC chip constituting a drive circuit of the image sensor are mounted is fitted, with signal cables being soldered to the circuit board of the imaging unit.

In recent years, there is a proposed technique in which an imaging unit and a peripheral circuit of a solid-state image sensor are arranged side-by-side on a front surface to reduce the length in the row direction of the solid-state image sensor so as to reduce the diameter of the imaging unit (refer to JP 2010-51538 A).

SUMMARY

An imaging unit may include: an optical system; a semiconductor package including an image sensor configured to generate an electric signal by receiving light incident from the optical system and by performing photoelectric conversion on the received light, and a connection electrode formed on a back surface; a cable; an electronic component; and a multi-layer substrate having a rectangular plate shape and including: a first electrode and a second electrode arranged side-by-side with each other on a front surface, the semiconductor package being mounted on the first electrode, and the cable being connected to the second electrode; and a third electrode on a back surface, the electronic component being mounted on the third electrode, wherein the multi-layer substrate includes walls on at least two opposing sides of the back surface, and the semiconductor package is disposed such that a light receiving surface of the image sensor is arranged horizontally with respect to the multi-layer substrate.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Figure 1:
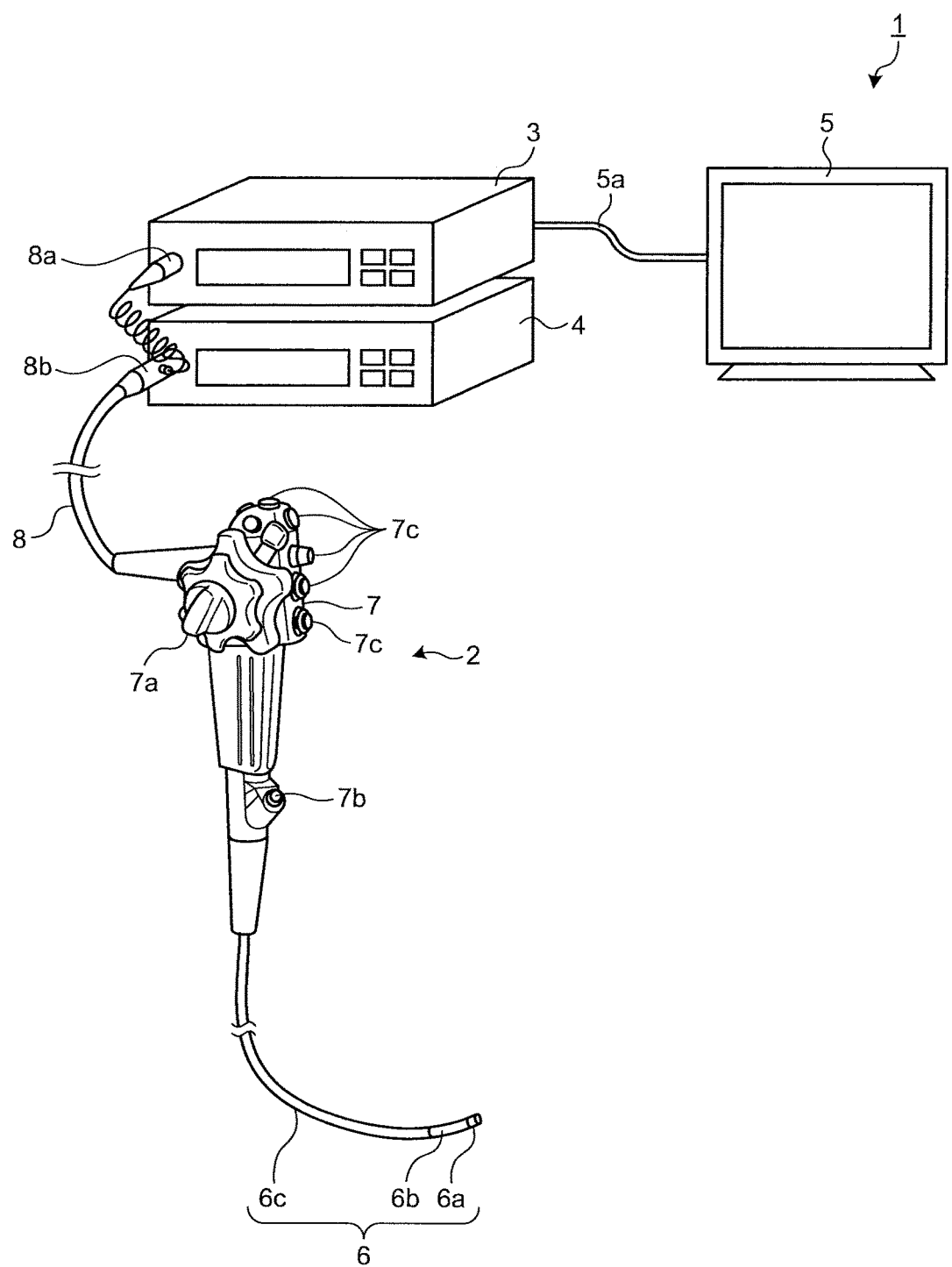
FIG. 1 is a block diagram schematically illustrating an overall configuration of an endoscope system according to a first embodiment.

Hereinafter, an endoscope system including an imaging unit will be described according to embodiments (hereinafter, referred to as "embodiment(s)"). Note that the present disclosure is not intended to be limited by these embodiments. In the drawings, same reference signs are attached to the same portions. Furthermore, it needs to be kept in mind that the drawings are schematic, and the relationship between the thickness and the width of individual members and the ratio between the members are different from an actual case. Still further, there are portions having different dimensions and ratios even between the drawings.

First Embodiment

FIG. 1 is a block diagram schematically illustrating an overall configuration of an endoscope system according to a first embodiment. As illustrated in FIG. 1, an endoscope system 1 according to the first embodiment includes an endoscope 2, an information processing apparatus 3, a light source apparatus 4, and a display device 5. The endoscope 2 is introduced into a subject and captures an image inside the body of a subject and generates an image signal of the interior of the subject. The information processing apparatus 3 performs predetermined image processing on the image signal captured by the endoscope 2 and controls each of portions of the endoscope system 1. The light source apparatus 4 generates illumination light for the endoscope 2. The display device 5 displays an image of the image signal after undergoing image processing by the information processing apparatus 3.

The endoscope 2 includes an insertion section 6, an operating unit 7, and a universal cord 8. The insertion section 6 is inserted into the subject. The operating unit 7 is arranged on a proximal end side of the insertion section 6 and gripped by an operator. The universal cord 8 has flexibility and extends from the operating unit 7.

The insertion section 6 is formed with an illumination fiber (light guide cable), an electric cable, an optical fiber, or the like. The insertion section 6 includes a distal end portion 6a, a bending portion 6b, and a flexible tube portion 6c. The distal end portion 6a includes an imaging unit described below. The bending portion 6b is a bendable portion formed with a plurality of bending pieces. The flexible tube portion 6c is flexible and provided on a proximal end side of the bending portion 6b. The distal end portion 6a includes an illumination unit, an observation unit, an opening portion, and an air/water feeding nozzle (not illustrated). The illumination unit illuminates an interior of the subject via an illumination lens. The observation unit captures the interior of the subject. The opening portion communicates with a treatment instrument channel.

The operating unit 7 includes a bending knob 7a, a treatment instrument insertion section 7b, and a plurality of switching sections 7c. The bending knob 7a is used to bend the bending portion 6b in up-down and left-right directions. The treatment instrument insertion section 7b is a section through which a treatment instrument such as biological forceps and a laser knife is inserted into the body cavity of the subject. Each of the switching sections 7c is used to operate peripheral equipment such as the information processing apparatus 3, the light source apparatus 4, an air feeding apparatus, a water feeding apparatus, and a gas feeding apparatus. A treatment instrument inserted from the treatment instrument insertion section 7b passes through an internal treatment instrument channel and comes out from an opening portion 6d of the distal end of the insertion section 6.

The universal cord 8 includes an illumination fiber and a cable. The universal cord 8 is branched at a proximal end. One end portion of the branched section is a connector 8a, and the other end portion is a connector 8b. The connector 8a is removably attached to the connector of the information processing apparatus 3. The connector 8b is removably attached to the light source apparatus 4. The universal cord 8 transmits illumination light emitted from the light source apparatus 4 to the distal end portion 6a via the connector 8b and the illumination fiber. Moreover, the universal cord 8 transmits an image signal captured by an imaging unit to be described below to the information processing apparatus 3 via the cable and the connector 8a.

The information processing apparatus 3 performs predetermined image processing on the image signal output from the connector 8a, while controlling the whole endoscope system 1.

The light source apparatus 4 is configured with a light source that emits light, a condenser lens, or the like. Under the control of the information processing apparatus 3, the light source apparatus 4 emits light from the light source and supplies the light to the endoscope 2 connected via the connector 8b and the illumination fiber of the universal cord 8, as illumination light supplied to the interior of the subject as an object.

The display device 5 includes a display using liquid crystal or organic electro luminescence (EL). The display device 5 displays, via a video cable 5a, various types of information including an image that has undergone predetermined image processing performed by the information processing apparatus 3. With this configuration, the operator may observe a desired position inside the subject and judge conditions by operating the endoscope 2 while viewing an image (in-vivo image) displayed by the display device 5.

Figure 2:
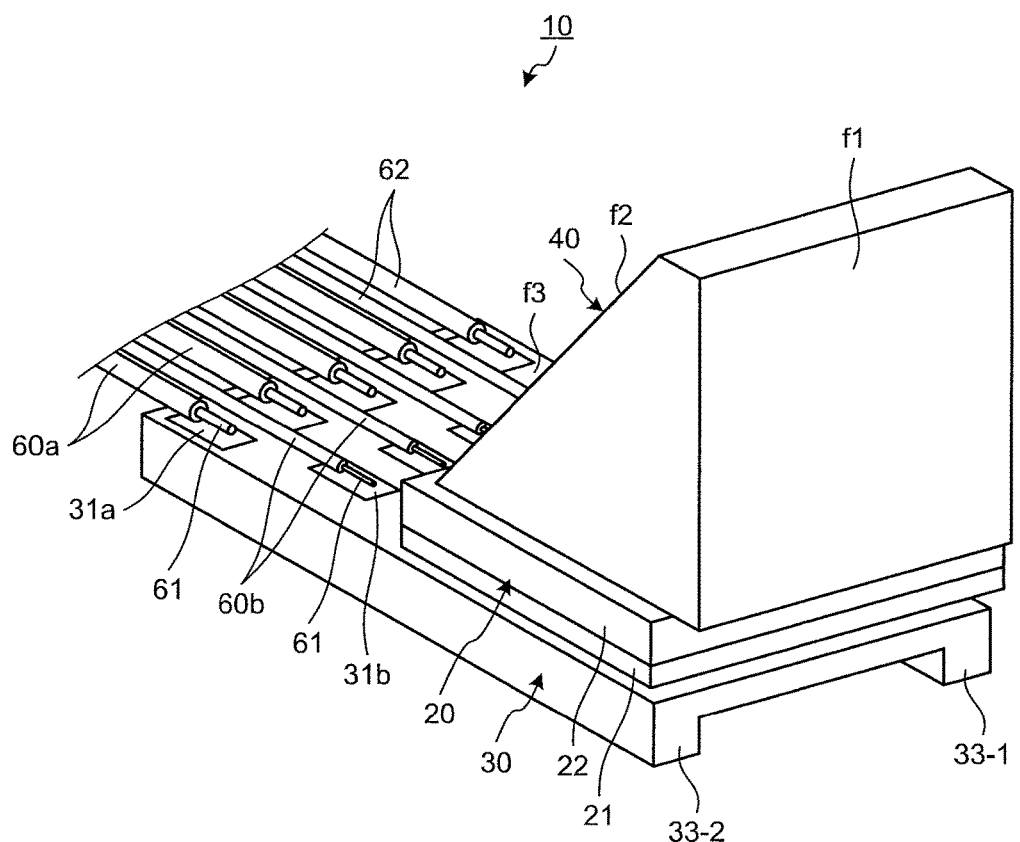
FIG. 2 is a perspective view of an imaging unit arranged at a distal end portion of the endoscope illustrated in FIG. 1.
Figure 3:
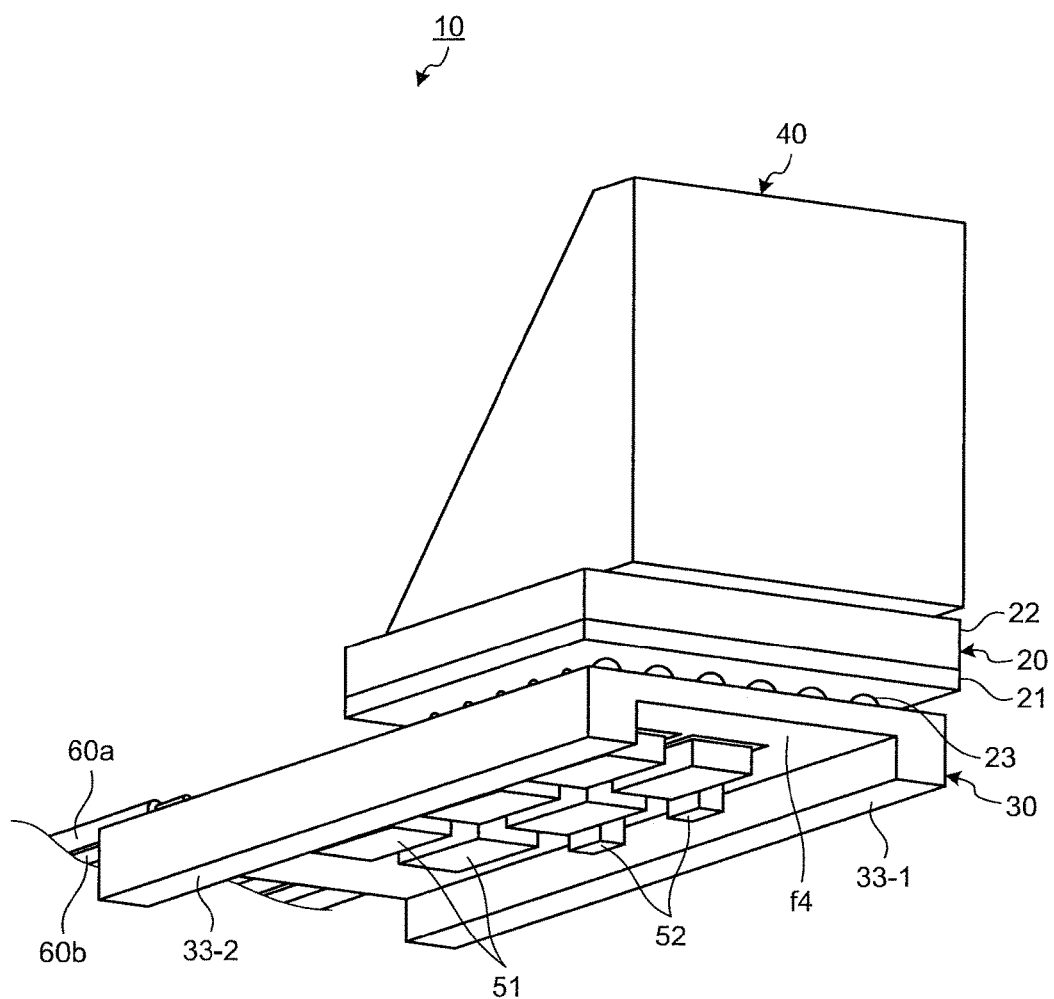
FIG. 3 is a perspective view of the imaging unit illustrated in FIG. 2 viewed from another direction.
Figure 4:
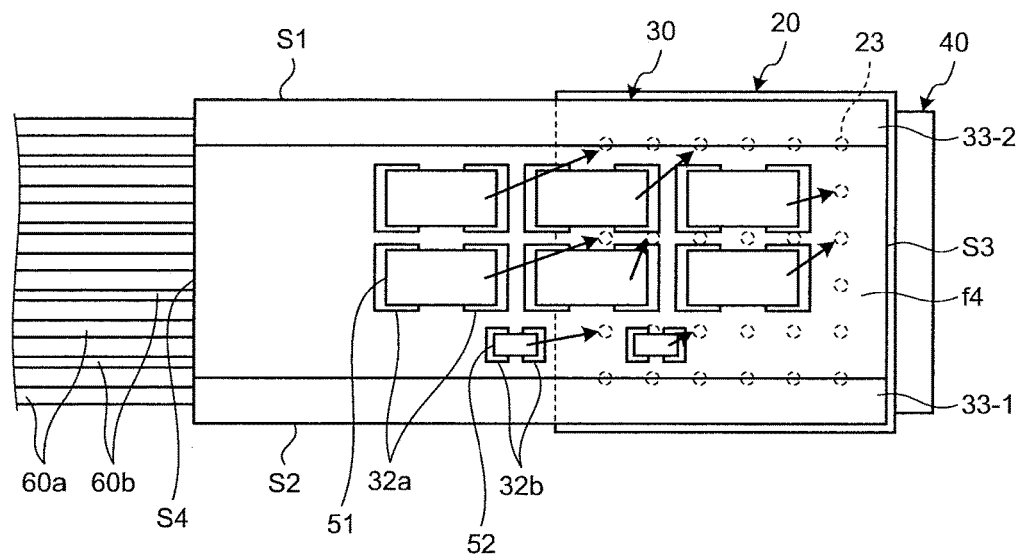
FIG. 4 is a bottom view of the imaging unit illustrated in FIG. 2.
Figure 5:
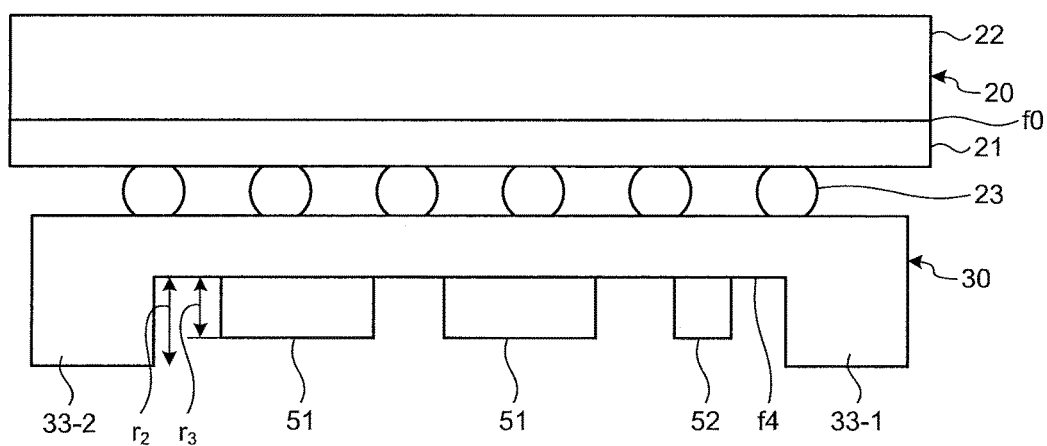
FIG. 5 is a partially enlarged side view of the imaging unit of FIG. 2 at a portion in the vicinity of the multi-layer substrate.
Figure 6:
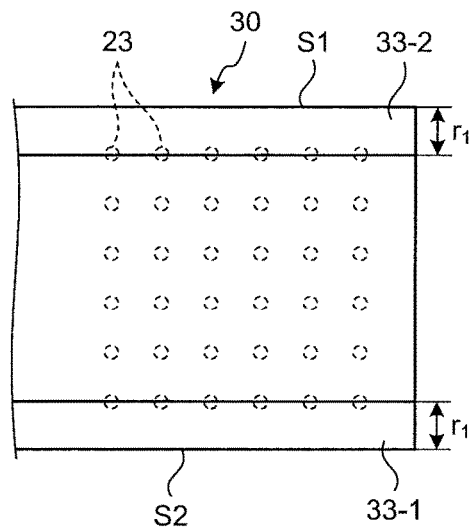
FIG. 6 is a diagram illustrating a positional relationship between a wall of the multi-layer substrate of FIG. 2 and bumps (connection electrodes of a semiconductor package)

Next, an imaging unit 10 used in the endoscope system 1 will be described in detail. FIG. 2 is a perspective view of the imaging unit 10 arranged at the distal end portion of the endoscope 2 illustrated in FIG. 1. FIG. 3 is a perspective view of the imaging unit 10 illustrated in FIG. 2 viewed from another direction. FIG. 4 is a bottom view of the imaging unit 10 illustrated in FIG. 2. FIG. 5 is a partially enlarged side view of the imaging unit 10 of FIG. 2 at a portion in the vicinity of a multi-layer substrate 30. FIG. 6 is a diagram illustrating a positional relationship between walls 33-1 and 33-2 of the multi-layer substrate 30 of FIG. 2 and bumps 23 (connection electrodes of a semiconductor package). Note that FIGS. 2 to 6 omit illustration of an underfill agent filled between a semiconductor package 20 and multi-layer substrate 30 and the solder used for connecting cables 60a and 60b and electronic components 51 and 52.

The imaging unit 10 includes a prism 40, a semiconductor package 20, a plurality of cables 60a and 60b, a plurality of electronic components 51 and 52, and a multi-layer substrate 30. The prism 40 collects and reflects incident light. The semiconductor package 20 includes an image sensor 21 that generates an electric signal by receiving the light incident from the prism 40 and performing photoelectric conversion on the received light, and includes connection electrodes formed on a back surface. The plurality of cables 60a and 60b transmits image signals from the image sensor 21 or supplies power supply voltage. The multi-layer substrate 30 has a rectangular plate shape and including, on a front surface f3, a first electrode on which the image sensor 21 is mounted and second electrodes 31a and 31b to which the cables 60a and 60b are connected being arranged side-by-side with each other, and including, on a back surface f4, third electrodes 32a and 32b on which the electronic components 51 and 52 are mounted.

The semiconductor package 20 has a structure in which glass 22 is attached to the image sensor 21. The light incident from a surface f1 of the prism 40 and reflected on a surface f2 is incident on a surface f0 (light receiving surface) of the image sensor 21 having the light receiving section, via the glass 22. Connection electrodes (not illustrated) and the bump 23 formed of solder, or the like, are formed on the back surface of a light receiving surface of the image sensor 21. It is preferable that the semiconductor package 20 is a chip size package (CSP) formed by performing wiring, electrode formation, resin encapsulation, and dicing on an image sensor chip in a wafer state, and that the size of the image sensor chip finally becomes the size of the semiconductor package chip. Moreover, the semiconductor package 20 is a landscape type, in which the surface f0 as the light receiving surface of the image sensor 21 is horizontally disposed.

On the front surface f3 of the multi-layer substrate 30, a first electrode on which the image sensor 21 is mounted and second electrodes 31a and 31b to which the cables 60a and 60b are connected are arranged side-by-side in a direction in which the cables 60a and 60b extend (hereinafter, referred to as optical axis direction). The cable 60a having a large diameter is mounted on the second electrode 31a arranged on the proximal end side of the multi-layer substrate 30 and the cable 60b having a small diameter is mounted on the second electrode 31b. Each of the cables 60a and 60b includes a conductor 61 and an outer casing 62 formed of an insulator for covering the conductor 61, with the outer casing 62 peeled off at the end portion to expose the conductor 61. The exposed conductor 61 is connected to each of the second electrodes 31a and 31b. The second electrode 31a and the second electrode 31b are arranged in a staggered pattern (zigzag shape) in order to reduce the diameter of the imaging unit 10 while increasing the mounting density of the cables 60a and 60b.

Examples of the multi-layer substrate 30 include a ceramic substrate, a glass epoxy substrate, a glass substrate, and a silicon substrate. From the viewpoint of increasing the reliability of connection with the semiconductor package 20, it is preferable to use those formed of a material having the same coefficient of thermal expansion as the material of the semiconductor package 20, for example, a silicon substrate and a ceramic substrate.

The multi-layer substrate 30 includes walls 33-1 and 33-2 on two opposing sides of the back surface f4, parallel to the optical axis direction illustrated in FIG. 4, that is, on opposing sides S1 and S2. The back surface f4 includes the third electrodes 32a and 32b on which the electronic components 51 and 52 are mounted. Three pairs of the third electrode 32a are arranged in two rows in parallel with the walls 33-1 and 33-2, and two pairs of the third electrode 32b are arranged in one row. Examples of the electronic components 51 and 52 to be mounted include passive components such as resistance coils, and active components such as driver ICs. As indicated by arrows in FIG. 4, the electronic components 51 and 52 are connected to the connection electrodes (bumps 23) of the semiconductor package 20 so as to shorten the wiring distance.

The walls 33-1 and 33-2 are formed over the entire lengths of the sides S1 and S2. As illustrated in FIG. 5, a height r2 of each of the walls 33-1 and 33-2 from the back surface f4 of the multi-layer substrate 30 is formed such that the upper surfaces of the electronic components 51 and 52 do not protrude from the back surface f4 of the multi-layer substrate 30 when the electronic components 51 and 52 are mounted on the third electrodes 32a and 32b, that is, the height r2 is formed to be higher than a height r3 of each of the electronic components 51 and 52 from the back surface f4 of the multi-layer substrate 30. The height r2 of the walls 33-1 and 33-2 is preferably set to about 0.2 mm to 0.3 mm, that is, about half the thickness of the multi-layer substrate 30 when the thickness of the multi-layer substrate 30 is about 0.4 mm to 0.5 mm.

Moreover, as illustrated in FIG. 6, a width r1 of each of the walls 33-1 and 33-2 is set to be a length that allows the connection electrodes (bumps 23) of the semiconductor package 20 adjacent to the sides S1 and S2 on which the walls 33-1 and 33-2 are arranged to overlap with the walls 33-1 and 33-2 in the vertical direction.

In the case of the semiconductor package 20 in which the connection electrodes (bumps 23) are arranged in a matrix, the influence of an outer peripheral portion of the connection electrodes (bumps 23) and the four corner portions of the connection electrodes (bumps 23) on the warping of the multi-layer substrate 30 is large. By arranging, however, the width r1 of the walls 33-1 and 33-2 to have a length to overlap with the connection electrodes (bumps 23) adjacent to the sides S1 and S2 of the semiconductor package 20, it is possible to increase the thickness of the multi-layer substrate 30 of the outer peripheral portion of the connection electrodes (bumps 23) and the four corner portions of the connection electrodes (bumps 23), leading to effective reduction of warping of the multi-layer substrate 30.

Although not illustrated in FIGS. 2 to 6, it is preferable that the connecting portions around the bump 23 between the semiconductor package 20 and the multi-layer substrate 30 are filled with an underfill agent. Moreover, it is preferable that encapsulation resin is filled at a portion in the vicinity of the connecting portion between the electronic components 51 and 52 mounted on the back surface f4 of the multi-layer substrate 30 and the third electrodes 32a and 32b. Since the type and filling amount of the underfill agent and the encapsulation resin influence the warping of the multi-layer substrate 30, it is preferable to determine the type, the filling amount, and arrangement so as to minimize the warping. It is preferable to use similar amounts of the underfill agent and the encapsulation resin having the same coefficient of thermal expansion.

While the first embodiment describes the case where the walls 33-1 and 33-2 have a rectangular column shape, the present disclosure is not limited thereto, and the upper portion may have a wavy or zigzag (saw tooth) shape. Moreover, there is no need to arrange the walls 33-1 and 33-2 over the entire lengths of the sides S1 and S2. For example, it is allowable to have a slit in the middle of the walls 33-1 and 33-2 as long as the walls cover main portions of the sides S1 and S2, for example, having the length of 50% or more, preferably 80% or more, of the length of the sides S1 and S2, and as long as the walls are arranged at corner portions of the multi-layer substrate 30.

In the first embodiment, by providing the walls 33-1 and 33-2 on the opposing sides S1 and S2 of the back surface f4 of the multi-layer substrate 30, it is possible to reduce the warping of the multi-layer substrate 30 and thus, to enhance reliability of connection between the semiconductor package 20 and the multi-layer substrate 30. Moreover, in a case where the electronic components 51 and 52 include a capacitor (decoupling capacitor), it is possible to arrange the decoupling capacitor in the immediate vicinity of the image sensor 21 via the multi-layer substrate 30 on which the semiconductor package 20 is mounted. This makes it possible to reduce the impedance between the image sensor 21 and the decoupling capacitor, and to achieve stable driving of the image sensor 21 while increasing the speed of the image sensor 21.

While the first embodiment uses the prism 40 as the optical system, it is also applicable to a side-view endoscope using a general objective lens.

Second Embodiment

Figure 7:
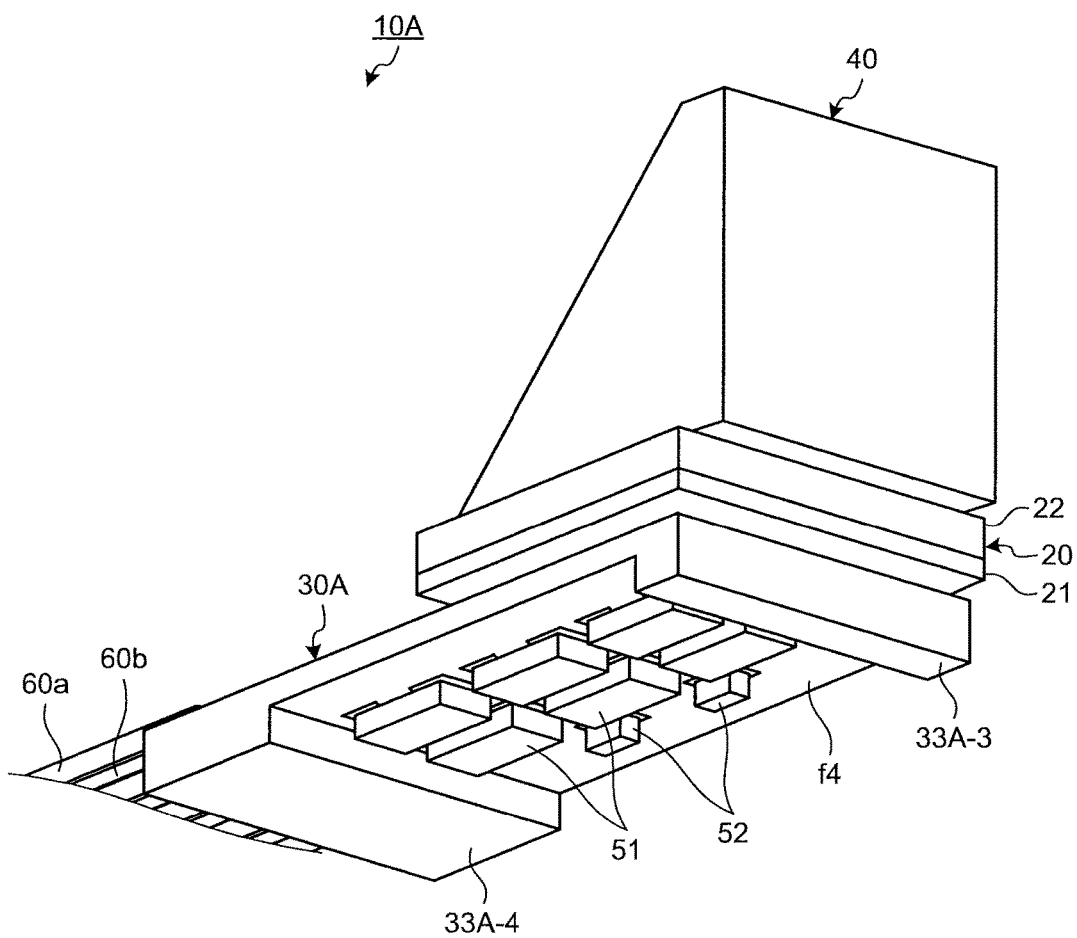
FIG. 7 is a perspective view of an imaging unit according to a second embodiment.
Figure 8:
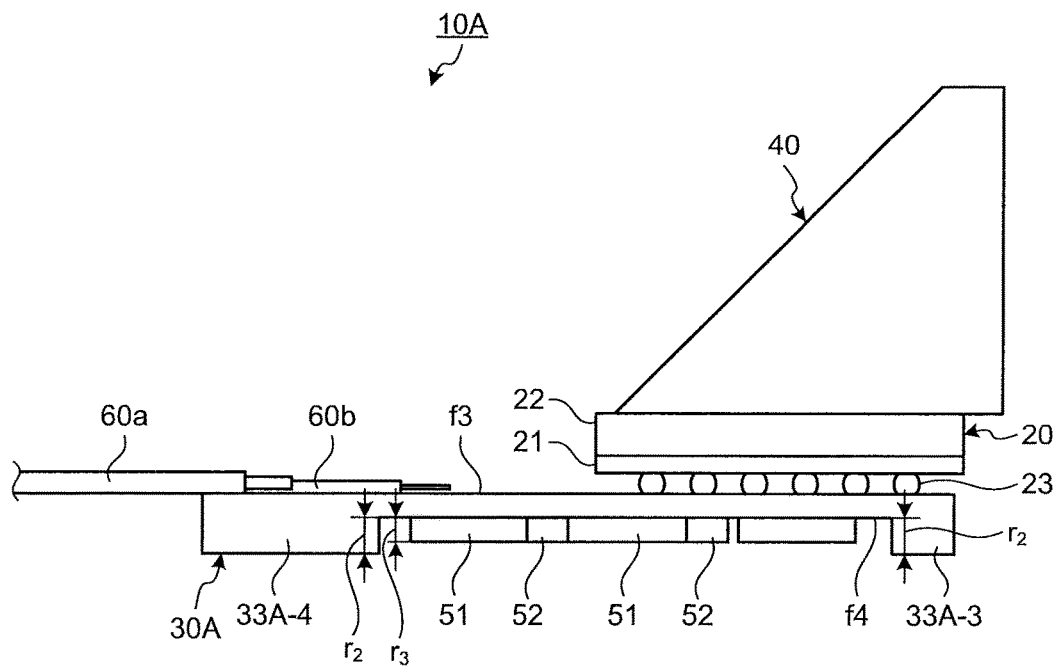
FIG. 8 is a side view of the imaging unit illustrated in FIG. 7.
Figure 9:
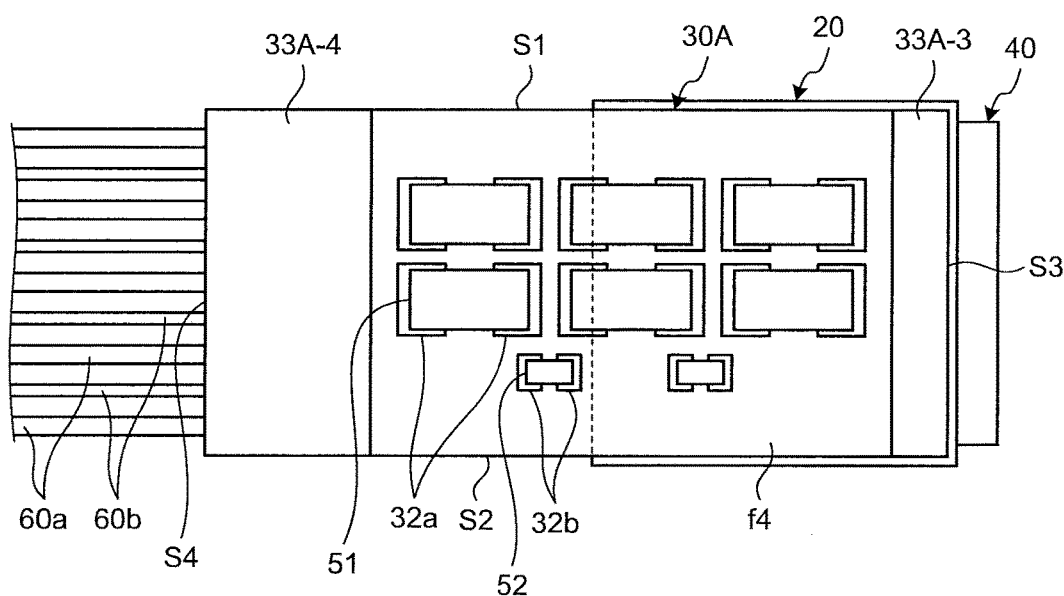
FIG. 9 is a bottom view of the imaging unit illustrated in FIG. 7.
Figure 10:
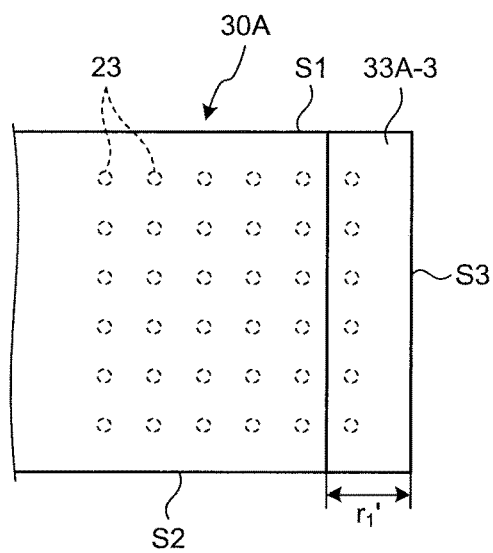
FIG. 10 is a diagram illustrating a positional relationship between a wall of the multi-layered substrate of FIG. 7 and bumps (connection electrodes of a semiconductor package)

In an imaging unit 10A according to a second embodiment, walls 33A-3 and 33A-4 are arranged on sides S3 and S4 perpendicular to the optical axis direction. FIG. 7 is a perspective view of the imaging unit 10A according to the second embodiment. FIG. 8 is a side view of the imaging unit 10A illustrated in FIG. 7. FIG. 9 is a bottom view of the imaging unit 10A illustrated in FIG. 7. FIG. 10 is a diagram illustrating a positional relationship between the walls 33A-3 and 33A-4 of a multi-layer substrate 30A of FIG. 7 and the bumps 23 (connection electrodes of a semiconductor package).

The imaging unit 10A includes walls 33A-3 and 33A-4 on two opposing sides of the back surface f4 of the multi-layer substrate 30A, specifically, the opposing sides S3 and S4 perpendicular to the optical axis direction illustrated in FIGS. 7 to 9.

The walls 33A-3 and 33A-4 are formed over the entire lengths of the sides S3 and S4. The height r2 of each of the walls 33A-3 and 33A-4 from the back surface f4 of the multi-layer substrate 30A is formed so as to be higher than the height r3 of each of the electronic components 51 and 52 from the back surface f4 of the multi-layer substrate 30A. As illustrated in FIG. 10, a width r1' of the wall 33A-3 has a length covering the connection electrodes (bumps 23) of the semiconductor package 20, adjacent to the side S3 on which the wall 33A-3 is arranged.

In the second embodiment, by providing the walls 33A-3 and 33A-4 on the opposing sides S3 and S4 of the back surface f4 of the multi-layer substrate 30A, it is possible to reduce the warping of the multi-layer substrate 30A and thus, to enhance reliability of connection between the semiconductor package 20 and the multi-layer substrate 30A.

Third Embodiment

Figure 11:
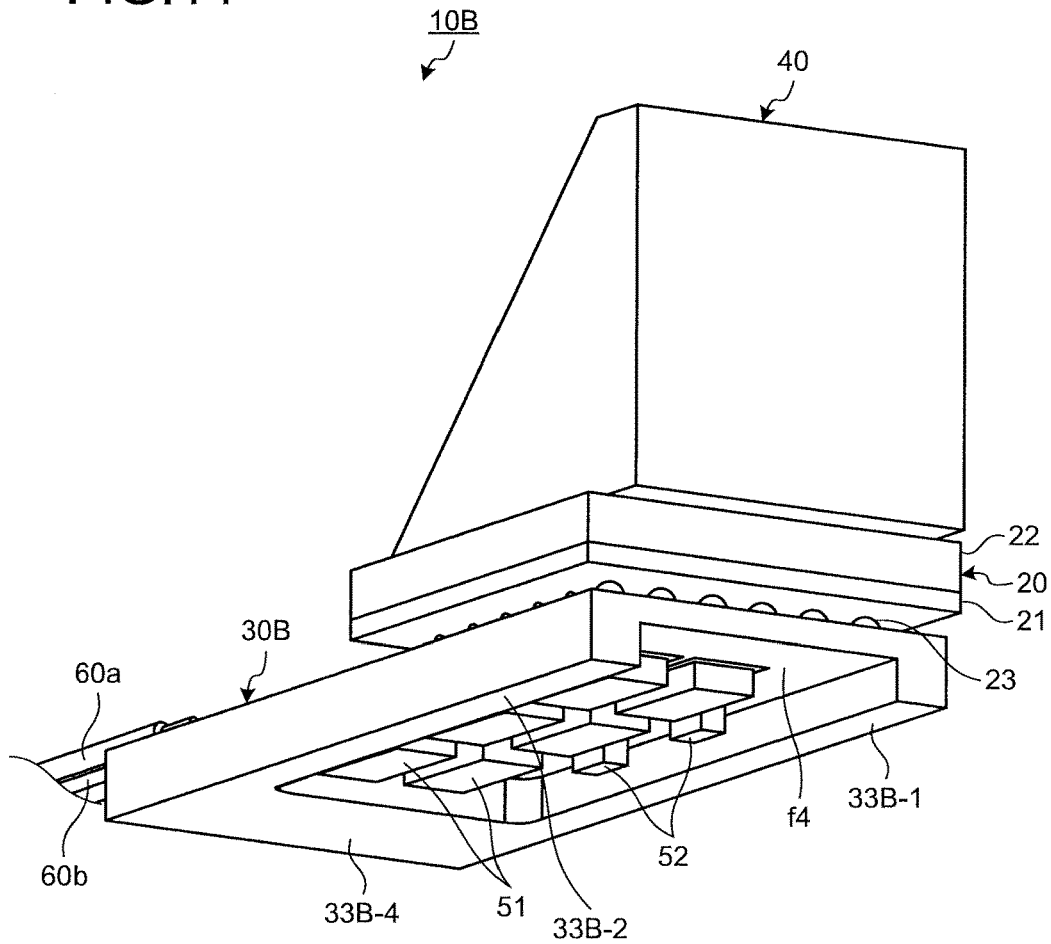
FIG. 11 is a perspective view of an imaging unit according to a third embodiment.
Figure 12:
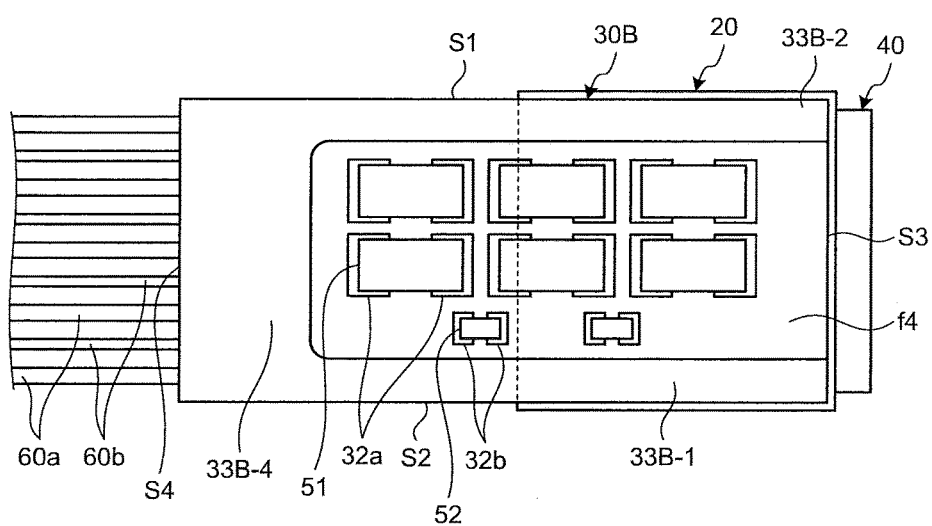
FIG. 12 is a bottom view of the imaging unit illustrated in FIG. 11.

In an imaging unit 10B according to a third embodiment, walls 33B-1, 33B-2, and 33B-4 are arranged on the sides S1 and S2 parallel to the optical axis direction, and on the side S4 perpendicular to the optical axis direction. FIG. 11 is a perspective view of the imaging unit 10B according to the third embodiment. FIG. 12 is a bottom view of the imaging unit 10B illustrated in FIG. 11.

The imaging unit 10B includes walls 33B-1, 33B-2, and 33B-4 on two opposing sides of the back surface f4 of a multi-layer substrate 30B, specifically, the opposing sides S1 and S2 parallel to the optical axis direction illustrated in FIGS. 11 and 12, and on the side S4 perpendicular to the optical axis direction.

The walls 33B-1, 33B-2, and 33B-4 are formed over the entire lengths of the sides S1, S2 and S4. The heights of the walls 33B-1, 33B-2, and 33B-4 from the back surface f4 of the multi-layer substrate 30B are formed so as to be higher than the heights of the electronic components 51 and 52 from the back surface f4 of the multi-layer substrate 30B. Moreover, similarly to the first embodiment, the width of each of the walls 33B-1 and 33B-2 is set to be a length to overlap with the connection electrodes (bumps 23) of the semiconductor package 20, adjacent to the sides S1 and S2 on which the walls 33B-1 and 33B-2 are arranged.

In the third embodiment, by providing the walls 33B-1, 33B-2, and 33B-4 on the opposing sides S1, S2, and S4 of the back surface f4 of the multi-layer substrate 30B, it is possible to reduce the warping of the multi-layer substrate 30B and thus, to enhance reliability of connection between the semiconductor package 20 and the multi-layer substrate 30B.

Fourth Embodiment

Figure 13:
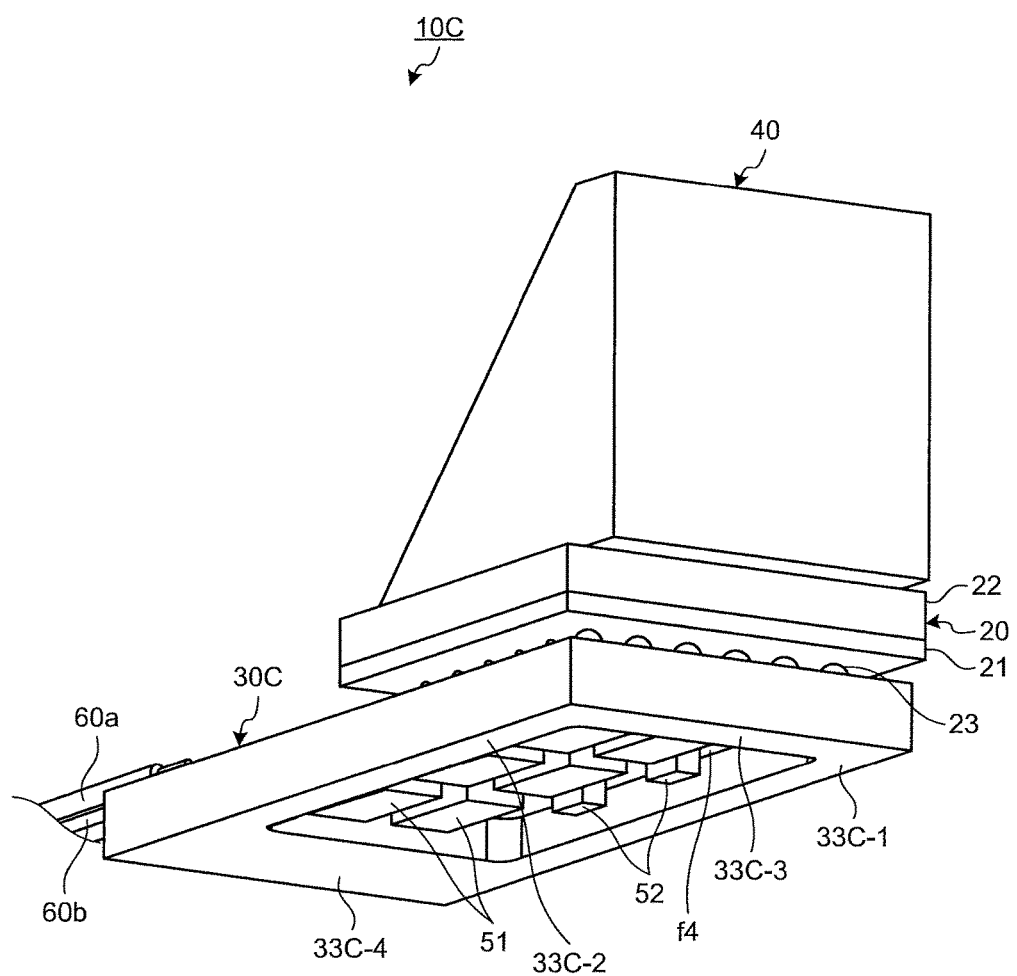
FIG. 13 is a perspective view of an imaging unit according to a fourth embodiment.
Figure 14:
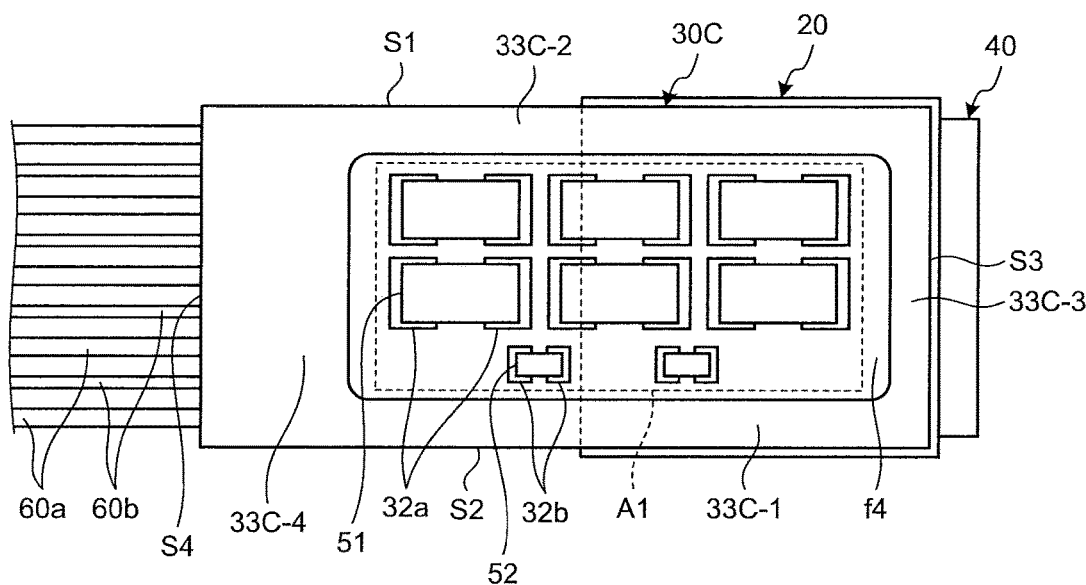
FIG. 14 is a bottom view of the imaging unit illustrated in FIG. 13.
Figure 15:
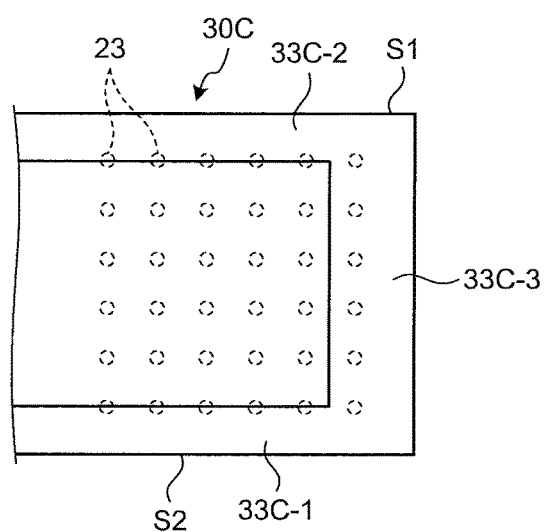
FIG. 15 is a diagram illustrating a positional relationship between a wall of the multi-layered substrate of FIG. 13 and bumps (connection electrodes of a semiconductor package)

In an imaging unit 10C according to a fourth embodiment, walls 33C-1, 33C-2, 33C-3, and 33C-4 are formed on the entire periphery of the back surface f4 of a multi-layer substrate 30C, that is, on the sides S1, S2, S3 and the side S4. FIG. 13 is a perspective view of the imaging unit 10C according to the fourth embodiment. FIG. 14 is a bottom view of the imaging unit 10C illustrated in FIG. 13. FIG. 15 is a diagram illustrating a positional relationship between the walls 33C-1, 33C-2, and 33C-3 of the multi-layer substrate 30C of FIG. 13 and the bumps 23 (connection electrodes of the semiconductor package).

In the imaging unit 100, walls 33C-1, 33C-2, 33C-3, and 33C-4 are provided on opposing sides S1, S2, S3, and S4 of the back surface f4 of the multi-layer substrate 30C.

The walls 33C-1, 33C-2, 33C-3, and 33C-4 are formed over the entire lengths of the sides S1, S2, S3 and S4, and an arrangement area A1 of the third electrodes 32a and 32b connecting the electronic components 51 and 52 is surrounded by the walls 33C-1, 33C-2, 33C-3, and 33C-4. The heights of the walls 33C-1, 33C-2, 33C-3, and 33C-4 from the back surface f4 of the multi-layer substrate 30C are formed so as to be higher than the heights of the electronic components 51 and 52 from the back surface f4 of the multi-layer substrate 30C.

Moreover, similarly to the first embodiment, the width of each of the walls 33C-1 and 33C-2 is set to be a length to overlap with the connection electrodes (bumps 23) of the semiconductor package 20, adjacent to the sides S1 and S2 on which the walls 33C-1 and 33C-2 are arranged. Moreover, the width of the wall 33C-3 has a length covering the connection electrodes (bumps 23) of the semiconductor package 20, adjacent to the side S3 on which the wall 33C-3 is arranged.

In the fourth embodiment, by providing the walls 33C-1, 33C-2, 33C-3, and 33C-4 on the entire periphery of the back surface f4 of the multi-layer substrate 30C, it is possible to reduce the warping of the multi-layer substrate 30C and thus, to enhance the reliability of connection between the semiconductor package 20 and the multi-layer substrate 30C.

In the above-described fourth embodiment, the third electrode 32a connecting the electronic component 51 and the second electrode 31b connecting the cable 60b are arranged so as to overlap with each other in the vertical direction. In this arrangement, depending on the types and the number of the electronic components to be mounted on the multi-layer substrate, it is preferable to have an arrangement such that the third electrodes 32a and 32b do not overlap with the second electrodes 31b connecting the cable 60b.

Figure 16:
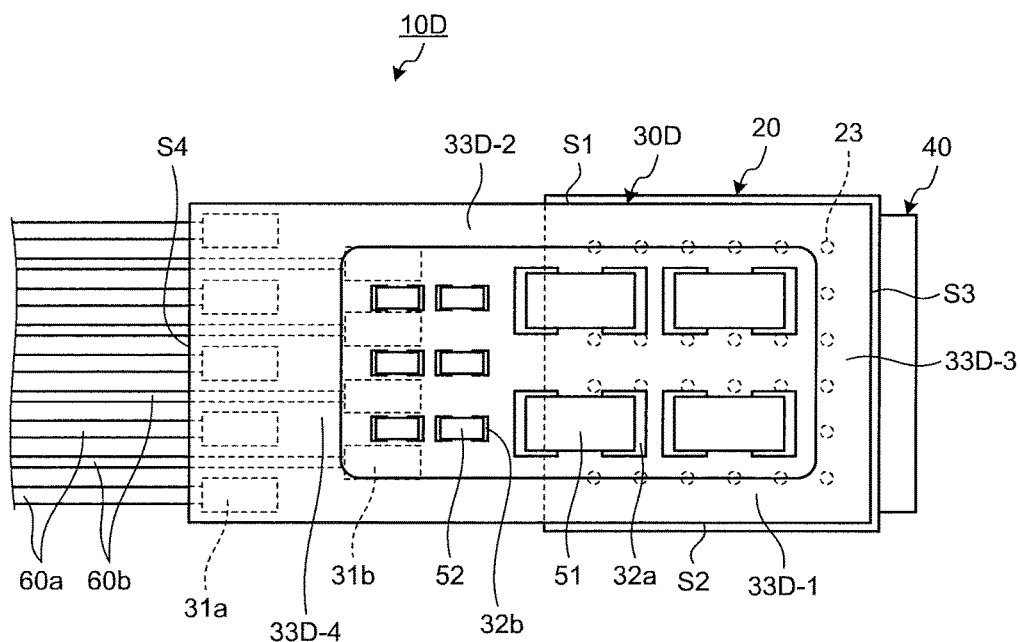
FIG. 16 is a bottom view of an imaging unit according to a first modification of the fourth embodiment.

FIG. 16 is a bottom view of an imaging unit 10D according to a first modification of the fourth embodiment. Similarly to the fourth embodiment, the imaging unit 10D has the walls 33D-1, 33D-2, 33D-3, and 33D-4 on the opposing sides S1, S2, S3, and S4 of the back surface f4 of a multi-layer substrate 30D. The heights of the walls 33D-1, 33D-2, 33D-3, and 33D-4 from the back surface f4 of the multi-layer substrate 30D are formed so as to be higher than the heights of the electronic components 51 and 52 from the back surface f4 of the multi-layer substrate 30D.

On the back surface f4 of the multi-layer substrate 30D, two pairs of the third electrode 32a for connecting the electronic components 51 are arranged in two rows in parallel with the walls 33D-1 and 33D-2 at a position on the side S3 side. Two pairs of the third electrodes 32b connecting the electronic components 52 are arranged in three rows on the side S4 side.

The third electrode 32b connecting the electronic component 52 arranged on the side S4 side is arranged so as not to overlap in the vertical direction with the second electrode 31b arranged on the center side of the front surface f3 of the multi-layer substrate 30D. In other words, while the third electrode 32b and the second electrode 31b overlap with each other in a direction perpendicular to the optical axis direction, they are arranged at positions not overlapping with each other when viewed in the optical axis direction. Moreover, the third electrode 32b is at a position not overlapping with the second electrode 31a in the vertical direction. Similarly, the third electrode 32a is at a position not overlapping with the second electrodes 31a and 31b in the vertical direction.

By arranging the third electrodes 32a and 32b and the second electrodes 31a and 31b so as not to overlap with each other in the vertical direction, it is possible to reduce thermal damage on the electronic components 51 and 52 when connecting the cables 60a and 60b to the second electrodes 31a and 31b. Moreover, it is possible to prevent remelting of the solder mounting portion of the electronic components 51 and 52. Furthermore, it is possible to increase the yield of the imaging unit 10D by the above-described effect.

Depending on the type and number of the electronic components to be mounted on the multi-layer substrate, it is preferable to have an arrangement such that the arrangement area of the third electrodes 32a and 32b does not overlap with the arrangement area of the second electrodes 31a and 31b.

Figure 17:
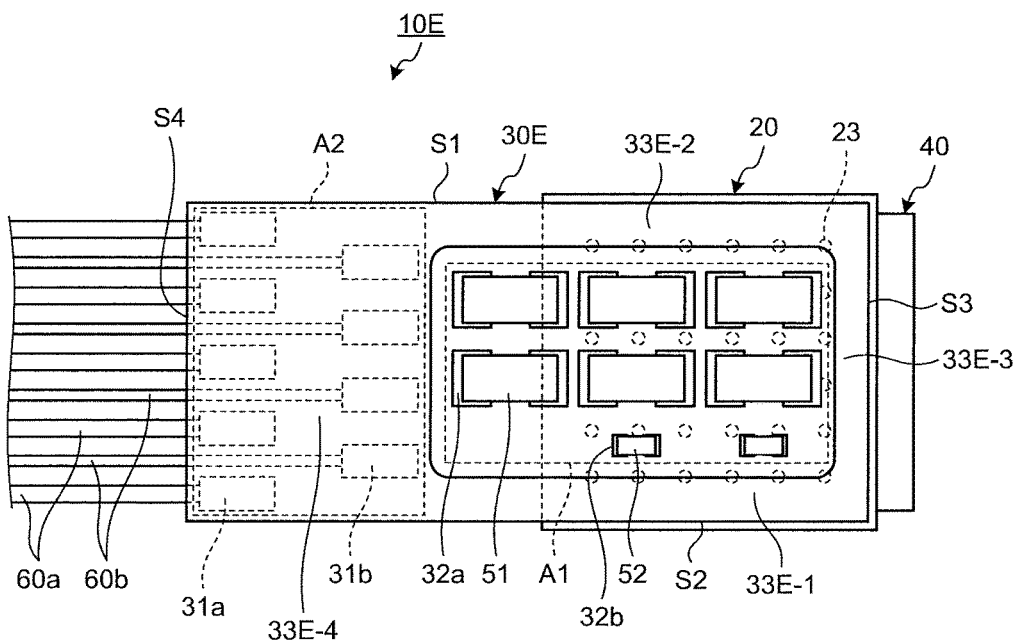
FIG. 17 is a bottom view of an imaging unit according to a second modification of the fourth embodiment.

FIG. 17 is a bottom view of an imaging unit 10E according to a second modification of the fourth embodiment. In the imaging unit 10E, the arrangement area A1 of the third electrodes 32a and 32b is arranged so as not to overlap in the vertical direction with an arrangement area A2 of the second electrodes 31a and 31b connecting the cables 60a and 60b. With this arrangement, it is possible to further reduce thermal damage on the electronic components 51 and 52 when connecting the cables 60a and 60b to the second electrodes 31a and 31b.

Depending on the type and the number of electronic components to be mounted on the multi-layer substrate, it is preferable that the arrangement area of the third electrodes 32a and 32b is within a projection plane of the semiconductor package 20 in the vertical direction.

Figure 18:
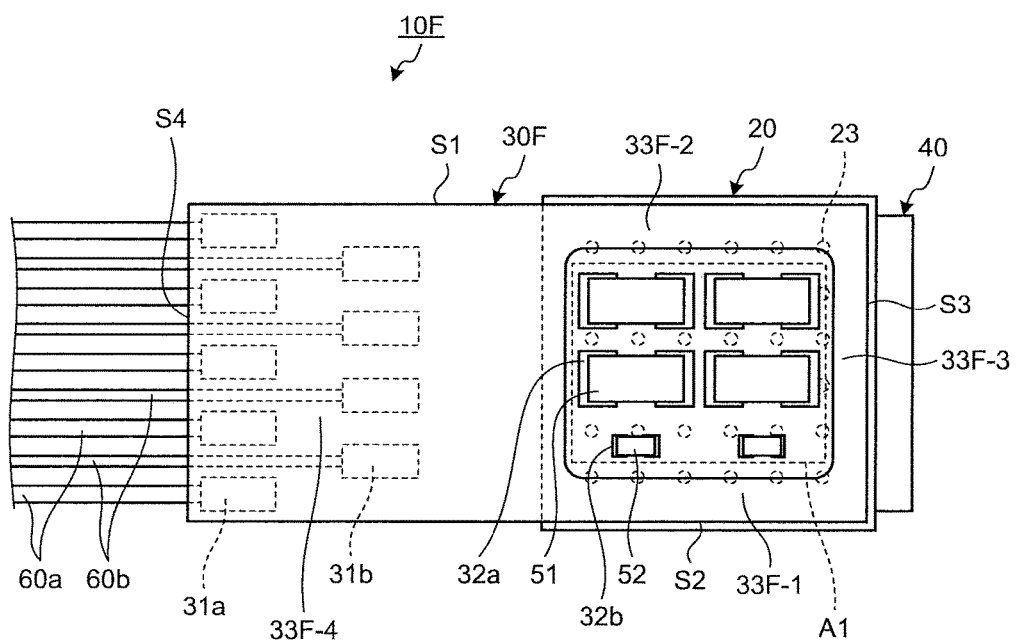
FIG. 18 is a bottom view of an imaging unit according to a third modification of the fourth embodiment.

FIG. 18 is a bottom view of an imaging unit 10F according to a third modification of the fourth embodiment. In the imaging unit 10F, the arrangement area A1 of the third electrodes 32a and 32b is arranged within the projection plane of the semiconductor package 20 in the vertical direction. This allows the electronic components 51 and 52 are to be arranged at a portion in the vicinity of the connection electrodes, making it possible to further stabilize driving of the image sensor 21. Moreover, with this arrangement, it is possible to further reduce thermal damage on the electronic components 51 and 52 when connecting the cables 60a and 60b to the second electrodes 31a and 31b.

Fifth Embodiment

Figure 19:
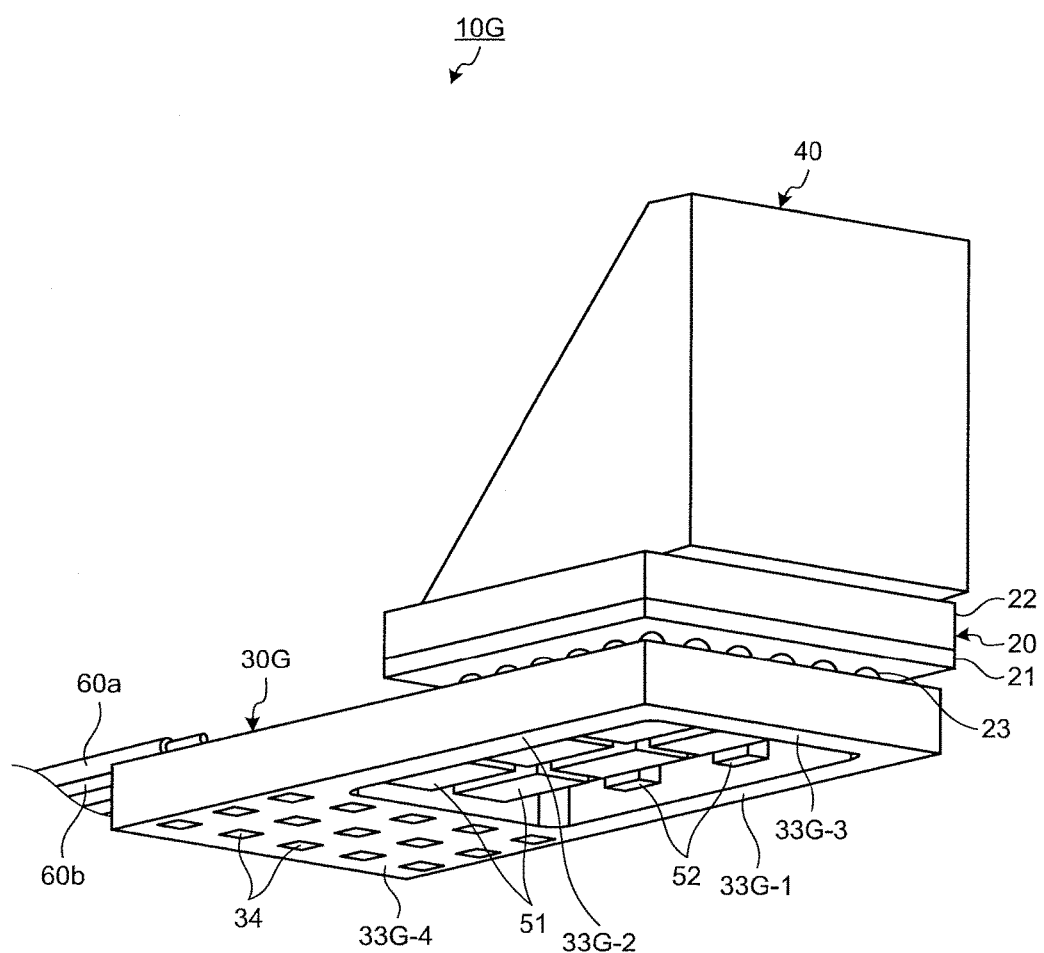
FIG. 19 is a perspective view of an imaging unit according to a fifth embodiment.
Figure 20:
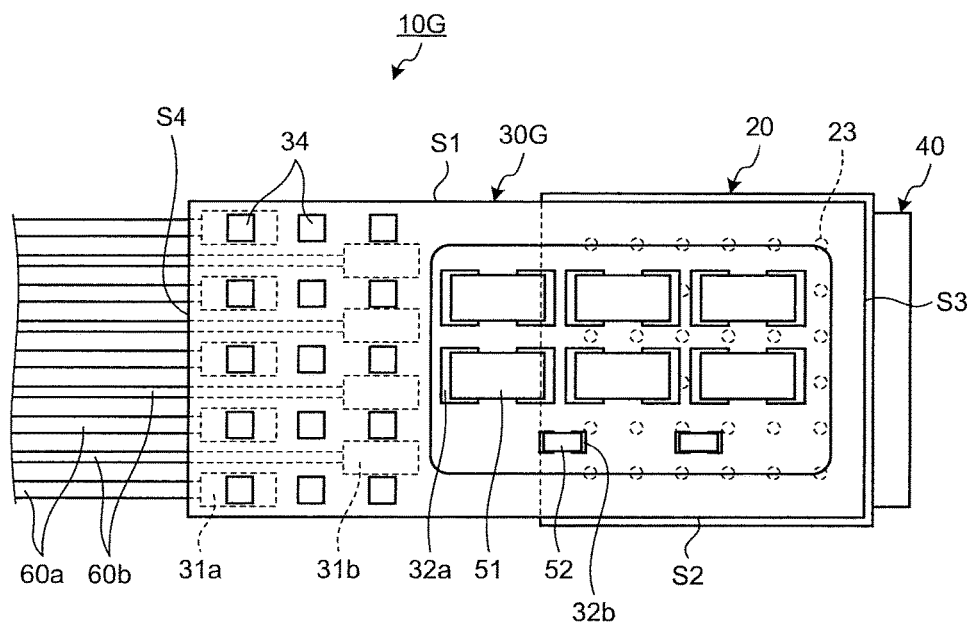
FIG. 20 is a bottom view of the imaging unit illustrated in FIG. 19.

An imaging unit 10G according to a fifth embodiment includes a wall on the side S4 and includes an inspection terminal 34 for inspection of an imaging unit 10G formed on a wall 33G-4 on the side S4 side. FIG. 19 is a perspective view of the imaging unit 10G according to the fifth embodiment. FIG. 20 is a bottom view of the imaging unit 10G illustrated in FIG. 19.

The imaging unit 10G includes walls 33G-1, 33G-2, 33G-3, and 33G-4 on opposing sides S1, S2, S3, and S4 on the back surface f4 of a multi-layer substrate 30G. The heights of the walls 33G-1, 33G-2, 33G-3, and 33G-4 from the back surface f4 of the multi-layer substrate 30G are formed so as to be higher than the heights of the electronic components 51 and 52 from the back surface f4 of the multi-layer substrate 30G.

The width of the wall 33G-4 on the side S4 side has a length to cover the back surface f4 side of the arrangement area of the second electrodes 31a and 31b formed on the front surface f3 side of the multi-layer substrate 30G. On the wall 33G-4, three pairs of the inspection terminals 34 for inspecting the imaging unit 10G are formed in five rows in parallel with the sides S1 and S2.

In the fifth embodiment, by providing the walls 33G-1, 33G-2, 33G-3, and 33G-4 on the sides S1, S2, S3, and S4 of the back surface f4 of the multi-layer substrate 30G, it is possible to reduce the warping of the multi-layer substrate 30G and thus, to enhance reliability of connection between the semiconductor package 20 and the multi-layer substrate 30G. Moreover, since the inspection terminal 34 is arranged on the wall 33G-4 of the back surface f4 of the multi-layer substrate 30G, it is possible to inspect the imaging unit 10G.

The imaging unit and the imaging module according to the present disclosure are useful in application to an endoscope system that demands an image with high image quality, reduction of diameter and length of the distal end portion.

According to the present disclosure, it is possible to prevent warping of the multi-layer substrate by providing the walls on the two opposing sides of the back surface of the multi-layer substrate, leading to achieving production of the imaging unit, the imaging module and the endoscope capable of achieving miniaturization and excellent reliability.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An imaging unit comprising:
an optical system;
a semiconductor package including
an image sensor configured to generate an electric signal by receiving light incident from the optical system and by performing photoelectric conversion on the received light, and
a connection electrode formed on a back surface;
a cable;
an electronic component; and
a multi-layer substrate having a rectangular plate shape and including:
a first electrode and a second electrode arranged side-by-side with each other on a front surface, the semiconductor package being mounted on the first electrode, and the cable being connected to the second electrode; and
a third electrode on a back surface, the electronic component being mounted on the third electrode,
wherein the multi-layer substrate includes walls on at least two opposing sides of the back surface,
the semiconductor package is disposed such that a light receiving surface of the image sensor is arranged horizontally with respect to the multi-layer substrate;

the walls are formed on at least a side of the multi-layer substrate from which the cable extends and a side opposed to the side, one of the walls forming a back surface side of an arrangement area of the second electrode of the multi-layer substrate, and an inspection terminal for inspecting the imaging unit is provided on the wall on the back surface side of the arrangement area of the second electrode.

2. The imaging unit according to claim 1, wherein a height of the walls is configured to prevent upper surfaces of the electronic components from protruding from the back surface of the multi-layer substrate when the electronic components are mounted on the third electrode.

3. The imaging unit according to claim 1, wherein a width of at least one wall of the walls has a length that allows the connection electrode adjacent to a side on which the at least one wall is arranged and at least a portion of the at least one wall to overlap with each other in a vertical direction.

4. The imaging unit according to claim 1, wherein the third electrode is arranged so as not to overlap with the second electrode in a vertical direction.

5. The imaging unit according to claim 4, wherein an arrangement area of the third electrode is arranged so as not to overlap with an arrangement area of the second electrode in the vertical direction.

6. The imaging unit according to claim 1, wherein the walls are formed on four sides of the back surface of the multi-layer substrate.

7. The imaging unit according to claim 1, wherein an arrangement area of the third electrode is within a projection plane of the semiconductor package in a vertical direction.

8. An endoscope apparatus comprising an insertion section including the imaging unit according to claim 1 provided at a distal end.

9. An imaging module comprising:
an optical system;
a semiconductor package including
   an image sensor configured to generate an electric signal by receiving light incident from the optical system and by performing photoelectric conversion on the received light, and
   a connection electrode formed on a back surface;
an electronic component; and
a multi-layer substrate having a rectangular plate shape and including:
   a first electrode and a second electrode arranged side-by-side with each other on a front surface, the semiconductor package being mounted on the first electrode, and a cable being connected to the second electrode; and
   a third electrode on a back surface, the electronic component being mounted on the third electrode,
wherein the multi-layer substrate includes walls on at least two opposing sides of the back surface,
the semiconductor package is disposed such that a light receiving surface of the image sensor is arranged horizontally with respect to the multi-layer substrate;
the walls are formed on at least a side of the multi-layer substrate from which the cable extends and a side opposed to the side, one of the walls forming a back surface side of an arrangement area of the second electrode of the multi-layer substrate, and
an inspection terminal for inspecting the imaging unit is provided on the wall on the back surface side of the arrangement area of the second electrode.

* * * * *